United States Patent [19]

Hata et al.

[11] 4,027,017
[45] May 31, 1977

[54] METHOD OF TREATING ALCOHOLISM

[75] Inventors: Shun-ichi Hata, Yokohama; Koji Mizuno, Tokorozawa; Yasuho Nishii, Niiza; Etsuko Mitsuishi, Tokyo; Motoharu Shiba, Ohmiya, all of Japan

[73] Assignee: Chugai Seiyaku Kabushiki Kaisha, Tokyo, Japan

[22] Filed: July 7, 1975

[21] Appl. No.: 593,444

[30]    Foreign Application Priority Data

July 16, 1974    Japan .............................. 49-80795

[52] U.S. Cl. ............................... 424/200; 424/180
[51] Int. Cl.$^2$ ...................................... A61K 31/675
[58] Field of Search ........................... 424/180, 200

[56]    References Cited
    OTHER PUBLICATIONS

Chemical Abstracts, 72:109720x (1970).
Chemical Abstracts, 60:4243e (1960).
Chemical Abstracts, 64:10328g (1966).

*Primary Examiner*—Leonard Schenkman
*Attorney, Agent, or Firm*—Browdy and Neimark

[57]    ABSTRACT

A pharmaceutical composition for treating alcoholism containing a uridine diphosphate glucuronic acid as an effective ingredient and a method of the use thereof are disclosed.

17 Claims, No Drawings

METHOD OF TREATING ALCOHOLISM

BACKGROUND OF THE INVENTION

This invention relates to a pharmaceutical composition and a method of use thereof; particularly it relates to a pharmaceutical composition containing a uridine diphosphate glucuronic acid as an effective ingredient for treatment of alcoholism and a method of use thereof.

Ethanol has been generally taken as an alcoholic drink, but it often causes acute and chronic alcoholism. The intake of a large amount of alcoholic drinks in a short period of time depresses the central nervous system and, thus, causes acute alcoholism such as drunkenness, dead drunkenness and coma. When taking a large amount of alcoholic liquor regularly becomes a habit, certain serious physical and mental disorders known as chronic alcoholism result. In these cases, it has been observed that the amount of neutral lipid accumulated in the liver is unusually high and this becomes a cause of liver disorder.

SUMMARY OF THE INVENTION

An object of the invention is to provide a pharmaceutical composition for treatment of alcoholism which comprises a uridine diphosphate glucuronic acid in an amount sufficient to realize treatment of alcoholism and a pharmaceutically acceptable carrier, and another object of this invention is to provide a method of treating alcoholism by the use of the pharmaceutical composition for treatment of alcoholism.

Other objects of this invention will be self-evident from the description hereinbelow.

DETAILED DESCRIPTION OF THE INVENTION

In accordance with this invention, alcoholism in human beings can be treated by the administration of a uridine diphosphate glucuronic acid.

One embodiment of this invention is a pharmaceutical composition for treatment of alcoholism which comprises a pharmaceutically acceptable carrier and as an effective ingredient, a uridine diphosphate glucuronic acid in an amount sufficient to realize the treatment of alcoholism.

In accordance with this embodiment, a uridine diphosphate glucuronic acid can be administered in the form of a preparation for oral administration or as a parenteral injection. For oral administration, tablet, granule, powder, suspension and lemonade are preferable, and the powder or granules may be put in capsules. The tablets, granules or powder are prepared by a conventional means from a uridine diphosphate glucuronic acid with a conventional pharmaceutically acceptable carrier such as lactose, starch, dextrine, sucrose, crystalline cellulose, kaolin, calcium carbonate, talc and the like. A suspension is prepared by suspending the uridine diphosphate glucuronic acid in an oil such as corn oil or olive oil, and lemonade is prepared by dissolving it in an aqueous solution of citric acid, tartaric acid or the like. For the preparation of parenteral injection, a uridine diphospate glucuronic acid is dissolved in an aqueous solution isotonized with sodium chloride, potassium chloride or the like and the solution is charged in an ampule and the ampule is melt-sealed. As an alternate method, the solution was placed in a vial and lyophilized. The amount of the uridine diphosphate glucoronic acid in the pharmaceutical composition should be in an amount sufficient to realize treatment of alcoholism. In general, in the preparation for oral administration, such as tablet, granule, powder, capsule, suspension or lemonade, the effective ingredient may be present in an amount of from 50 to 7,000 mg. preferably 100 to 700 mg per dose. On the other hand, for parenteral injection, the active ingredient may be present in an amount of from 50 to 1,500 mg, preferably 100 to 700 mg per dose.

The uridine diphosphate glucuronic acids which are useful for this invention are uridine-5'-diphosphate gluculonic acid and uridine-3'-diphosphate glucuronic acid, and they may be the free form or a metallic salt form, the metal being preferably sodium, potassium, lithium or the like.

The pharmaceutical composition for treatment of alcoholism is useful not only for acute alcoholism but also for chronic alcoholism.

Another embodiment of this invention is a method for treating alcoholism in human beings by the administration of a pharmaceutical composition for treatment of alcoholism comprising an effective amount of a uridine diphosphate glucuronic acid and a pharmaceutically acceptable carrier.

In accordance with this embodiment, a pharmaceutical composition described in the first embodiment of this invention is used as it is and the method comprises administering the composition orally or by injection or any other proper route to human beings.

That is, the treatment of acute alcoholism may be realized by oral administration of the pharmaceutical composition defined above, such as tablet, granule, powder, capsule, suspension or lemonade, or by intravenous or intramuscular injection of the composition in the form of parenteral injection just before or at the time of intake of alcoholic drinks. In order to treat acute alcoholism, such as drunkenness, dead drunkenness or coma, the pharmaceutical composition is administered orally by the use of the preparation for oral administration, or intravenously or intramuscularly by the use of the preparation for parenteral injection. In this case, the administration of the composition may be repeated every several hours to keep uridine diphosphate glucuronic acid in blood at a high level with better results.

Since a uridine diphosphate glucuronic acid is very low in toxicity on human beings, a considerable amount of the active ingredient may be administered for treatment of acute alcoholism. However, from safety and economic aspects it is advantageous to administer the active ingredient in an amount orally 400 mg/kg.body weight per day or 40 mg/kg.body weight per day by the parental injection.

The method for treating acute alcoholism in accordance with this invention can be applied for treating chronic alcoholism. In other words, treating acute alcoholism by the use of the pharmaceutical composition according to this invention is effective to treat chronic alcoholism. Since it is very difficult to have chronic alcoholic abstain from alcoholic drinks and the adminstration of the composition prevents the worsening the symptoms of chronic alcoholism, the composition, therefore, can also be used for the treatment of chronic alcoholism.

When the pharmaceutical composition of this invention is used for the purpose of treating alcoholism, the accumulation of neutral lipids in liver which are to be observed during alcoholism is inhibited and also alcohol level in blood is not increased rapidly. When the composition is used for the treatment, the alcohol level in blood is reduced effectively to ease drunkenness, dead drunkenness or coma.

This invention is further illustrated by the following Examples, but they are not to be construed as limiting the scope of this invention.

EXAMPLE 1

Inhibiting Action for Accumulation of Neutral Lipid in Liver

The Sprague Dawley strain male rats weighing 180+30 g which had been fed rat food commercially available as CLEA CE-2 and prevented from eating food for 16 hours just before the experiment was started were divided into groups of 10 rats each. Each rat was orally administered with trisodium uridine-5'-diphosphate glucuronic acid (UDPGA-3Na) as a suspension in corn oil in a dose of 160 mg/kg.body weight. Thirty minutes after the administration, each rat was orally administered with ethanol as a 50% aqueous solution in a dose of 6 g/kg.body weight and, 24 hours after the administration, the liver was taken out and an amount of neutral lipid contained therein was determined by the Van Handel and Zilver-Smit method. For control, a glucose aqueous solution having a caloric content equivalent to the same amount of ethanol was used instead of ethanol.

The results are shown in Table 1.

EXAMPLE 2

The Sprague Dawley strain male rats weighing 260+30 g which had been fed rat food commerically available as CLEA CE-2 and prevented from eating food for 12 hours just before the experiment were divided into groups each of 10–13 members each. Each rat was orally administered trisodium uridine-5'-diphosphate glucuronic acid (UDPGA.3Na) in the form of a suspension in corn oil in an amount 160 mg/kg.body weight. Thirty minutes after the administration, ethanol as a 50% aqueous solution was orally administered in a dose of 6 g/kg.body weight and then behavior of the rat was observed over 24 hours.

The results obtained are shown in Table 2.

Table 2

| Administration | Time after the administration of alcohol (hrs.) | Behaviour | | | Righting Reflex | |
| --- | --- | --- | --- | --- | --- | --- |
| | | Deep Sleep (heads) | Lying Flat (heads) | Normal Walking (heads) | − (heads) | + (heads) |
| Corn oil + Ethanol | 3 | 4 | 3 | 3 | 5 | 5 |
| | 6 | 4 | 4 | 2 | 5 | 5 |
| | 9 | 2 | 5 | 3 | 2 | 8 |
| | 12 | 0 | 1 | 9 | 0 | 10 |
| | 18 | 0 | 0 | 10 | 0 | 10 |
| UDPGA.3Na + Ethanol | 3 | 2 | 4 | 4 | 3 | 7 |
| | 6 | 2 | 6 | 2 | 3 | 7 |
| | 9 | 1 | 6 | 3 | 1 | 9 |
| | 12 | 0 | 0 | 10 | 0 | 10 |
| | 18 | 0 | 0 | 10 | 0 | 10 |

EXAMPLE 3

The Sprague Dawley strain male rats weighing 160+30 g which were fed rat food commercially available as CLEA CE-2 and prevented from eating food for 12 hours just before the experiment was started. Each rat was administered with ethanol as a 50% aqueous solution in a dose of 6 g/kg.body weight. Thirty minutes after the administration, the rat was orally administered with a suspension of trisodium uridine-5'-diphosphate glucuronic acid (UDPGA.3Na) in corn oil in a dose of 160 mg/kg.body weight based on UDPGA.3Na. The behavior of the rat was observed over 24 hours after the last administration.

The results obtained are shown in Table 3.

Table 3

| Administration | Time after the administration of alcohol (hrs.) | Behaviour | | | Righting Reflex | |
| --- | --- | --- | --- | --- | --- | --- |
| | | Deep Sleep (heads) | Lying Flat (heads) | Normal Walking (heads) | − (heads) | + (heads) |
| Ethanol + Corn oil | 3 | 3 | 5 | 0 | 3 | 5 |
| | 6 | 5 | 3 | 0 | 5 | 3 |
| | 9 | 3 | 3 | 2 | 2 | 6 |
| | 12 | 0 | 2 | 6 | 0 | 8 |
| | 18 | 0 | 0 | 8 | 0 | 8 |
| Ethanol + UDPGA.3Na | 3 | 2 | 5 | 3 | 3 | 7 |
| | 6 | 2 | 6 | 2 | 3 | 7 |
| | 9 | 1 | 3 | 6 | 2 | 8 |
| | 12 | 0 | 2 | 8 | 0 | 10 |
| | 18 | 0 | 0 | 10 | 0 | 10 |

Table 1

| Administration | Neutral Lipid in Liver (mg/g) | % inhibition |
| --- | --- | --- |
| Corn oil + Glucose | 11.47±4.99 | — |
| Corn oil + Ethanol | 40.27±9.25 | — |
| UDPGA.3Na + Ethanol | 23.05±10.72 | 59.7 |

EXAMPLE 4

Measurement of Alcohol Level in Blood

In this Example, Sprague Dawley strain female rats (weighing 150±20 g) divided into groups of 9–12 members each were used.

After abstention from food overnight each rat was orally administered trisodium uridine-5´-diphosphate glucuronic acid (UDPGA.3Na) in the form of a physiological saline solution in a dose of 160 mg/kg.body weight as an effective ingredient and, 30 minutes after the administration, the rat was administered with ethanol in a dose of 6 g/kg body weight. Four hours and thirty minutes after the administration of ethanol, the rat was etherized, and blood was sampled from its heart to determine alcohol level in the blood by a alcoholic dehydrogenase method. For control, a physiological saline solution was used instead of the UDPGA.3Na solution.

The results are shown in Table 4 from which the alcohol level in blood of the rat administered with UDPGA.3Na is significantly lowered in comparison with the control.

Further, it was found that the alcohol level in blood almost completely correlates closely with the changes in behavior symptoms.

Table 4

| Group | Test Animal Number | Ethanol level in Blood (mg/ml) | Behavior |
| --- | --- | --- | --- |
| Control | 1 | 1.05 | normal walking |
|  | 2 | 2.94 | deep sleep, lying on the side |
|  | 3 | 3.09 | " |
|  | 4 | 3.87 | " |
|  | 5 | 3.48 | " |
|  | 6 | 2.79 | " |
|  | 7 | 2.79 | " |
|  | 8 | 3.24 | " |
|  | 9 | 4.18 | " |
|  | Average | 3.05±0.84* |  |
| UDPGA.3Na Administration | 1 | 2.21 | lying flat |
|  | 2 | 1.65 | normal walking |
|  | 3 | 1.82 | " |
|  | 4 | 1.41 | " |
|  | 5 | 1.19 | " |
|  | 6 | 2.15 | " |
|  | 7 | 0.85 | " |
|  | 8 | 0.37 | " |
|  | 9 | 0.63 | " |
|  | 10 | 1.79 | " |
|  | 11 | 2.19 | lying flat |
|  | 12 | 2.82 | deep sleep |
|  | Average | 1.59±0.93* |  |

*Confidence Limits: 98%

EXAMPLE 5

Preparation of Pharmaceutical Composition a. Capsules

Pulverised trisodium uridine-5´-diphosphate glucuronic acid (435 g) was thoroughly mixed with lactose (63 g) and magnesium stearate (2 g), and hard gelatin capsules (No. 1) were filled with 500 mg each of the mixture.

b. Powder

Pulverized trisodium uridine-5´-diphosphate glucuronic acid (362 g) was thoroughly mixed with lactose (137 g) and magnesium stearate (1 g) to obtain a powder.

c. Tablets i. Pulverized trisodium uridine-5´-diphosphate glucuronic acid (145 g) was thoroughly mixed with lactose (28 g), crystalline cellulose (20 g), corn starch (5 g) and magnesium stearate (2 g). The mixture was formed by a tablet machine into tablets each 8 mm in diameter and weighing 200 mg.

ii. Pulverized tripotassium uridine-5´-diphosphate glucuronic acid passed through 50 mesh screen (290 g) was mixed with lactose (173 g) and calcium carboxymethylcellulose (20 g). To the mixture was added an aqueous paste of 4 g of corn starch followed by kneading it to form dough. The dough was fed to an extrusion type granulator to form granules. After drying the granules, they were passed through 14 mesh of screen and mixed with magnesium stearate (3 g). The mixture was formed by a tabletting machine into tablets each weighing 450 mg and being 12 mm in diameter.

d. Parenteral Injections

Monopotassium phosphate (3.6 g), disodium phosphate in the form of $Na_2HPO_4.12H_2O$ (14.4 g) and trisodium uridine-5´-diphosphate glucuronic acid (86 g) were dissolved in distilled water for parenteral injection (1 lit.), and the solution was charged in colorless ampules each 2 ml in volume. The ampules charged were melt-sealed and after the ampules were melt-sealed, sterilized at 100° C for 30 minutes. The resulting parenteral injection which contained approximately 72 mg/ml of trisodium uridine-5´-diphosphate glucuronic acid and had a pH 7.0 did not cause any pain on administration.

What is claimed is:

1. A method of reducing the alcohol content of the blood and the accumulation of neutral lipids in the liver following the intake of alcoholic drinks, which comprises orally administering to a patient in need of said therapy a pharmaceutical composition comprising an effective amount of a uridine diphosphate glucuronic acid as an active ingredient, and a pharmaceutically acceptable carrier, just before or at the time of intake of alcoholic drinks.

2. A method as set forth in claim 1 wherein said uridine diphosphate glucuronic acid is uridine-5´-diphosphate glucuronic acid or a metallic salt thereof.

3. A method as set forth in claim 2 wherein said metallic salt is selected from the group consisting of sodium, potassium and lithium salts.

4. A method as set forth in claim 1 wherein said uridine diphosphate glucuronic acid is uridine-3´-diphosphate glucuronic acid or a metallic salt thereof.

5. A method as set forth in claim 4 wherein said metallic salt is selected from the group consisting of sodium, potassium and lithium salts.

6. A method as set forth in claim 1 wherein said pharmaceutical composition is in a form of tablet, granule, powder, capsule, suspension or lemonade.

7. A method as set forth in claim 1 wherein the administration of said uridine diphosphate glucuronic acid is made in a dose of from 50 to 7,000 mg.

8. A method as set forth in claim 1 wherein the administration of said uridine diphosphate glucuronic acid is made in a dose of from 100 to 700 mg.

9. A method as set forth in claim 1 wherein said pharmaceutical composition is adminstered several times a day the total amount per day being a maximum of 400 mg/kg. body weight based on the active ingredient.

10. A method of reducing the alcohol content of the blood and the accumulation of neutral lipids in the liver following the intake of alcoholic drinks, which comprises intravenously or intramuscularly injecting in a patient in need of such therapy a pharmaecutical composition in the form of a parenteral injection comprising an effective amount of a uridine diphosphate glucuronic acid as an active ingredient and a pharmaceutically acceptable carrier, just before or at the time of intake of alcoholic drinks.

11. A method as set forth in claim 10 wherein the administration of said uridine diphosphate glucuronic acid is made in a dose of from 50 to 1,500 mg.

12. A method as set forth in claim 10 wherein the administration of said uridine diphosphate glucuronic acid is made in a dose of from 100 to 700 mg.

13. A method as set forth in claim 10 wherein the uridine diphosphate glucuronic acid is uridine-5'-diphosphate glucuronic acid or a metallic salt thereof.

14. A method as set forth in claim 13 wherein said metallic salt of uridine-5'-diphosphate glucuronic acid is selected from the group consisting of sodium, potassium and lithium salts.

15. A method as set forth in claim 10 wherein the uridine diphosphate glucuronic acid is uridine-3'-diphosphate glucuronic acid or a metallic salt thereof.

16. A method as set forth in claim 15 wherein said metallic salt of uridine-3'-diphosphate glucuronic acid is selected from the group consisting of sodium, potassium and lithium salts.

17. A method as set forth in claim 10 wherein said pharmaceutical composition is administered several times a day the total amount per day being a maximum of 40 mg/kg. body weight based on the active ingredient.

* * * * *

UNITED STATES PATENT AND TRADEMARK OFFICE
CERTIFICATE OF CORRECTION

PATENT NO. : 4,027,017
DATED : May 31, 1977
INVENTOR(S) : HATA et al

It is certified that error appears in the above-identified patent and that said Letters Patent are hereby corrected as shown below:

Column 3, line 13, "180+30g" should read --180$\pm$30g--

Column 4, line 4, "260+30g" should read --260$\pm$30g--

Column 4, line 35, "160+30g" should read --160$\pm$30g--

Column 5, line 2, "uridine-5-diphos-" should read --uridine-5'-diphos- --

Signed and Sealed this

*Fourth* Day of *October 1977*

[SEAL]

*Attest:*

RUTH C. MASON
*Attesting Officer*

LUTRELLE F. PARKER
*Acting Commissioner of Patents and Trademarks*